(12) United States Patent
Tkacik et al.

(10) Patent No.: US 7,108,791 B2
(45) Date of Patent: Sep. 19, 2006

(54) HIGH-RESOLUTION VIRUS REMOVAL METHODOLOGY AND FILTRATION CAPSULE USEFUL THEREFOR

(75) Inventors: Gabriel Tkacik, Bedford, MA (US); Greg Kazan, Danvers, MA (US)

(73) Assignee: Millipore Corporation, Billerica, MA (US)

( * ) Notice: Subject to any disclaimer, the term of this patent is extended or adjusted under 35 U.S.C. 154(b) by 154 days.

(21) Appl. No.: 10/145,939

(22) Filed: May 15, 2002

(65) Prior Publication Data
US 2002/0175124 A1    Nov. 28, 2002

Related U.S. Application Data

(63) Continuation-in-part of application No. 09/662,410, filed on Sep. 14, 2000, now abandoned.

(60) Provisional application No. 60/153,830, filed on Sep. 14, 1999.

(51) Int. Cl.
*B01D 61/00*    (2006.01)
(52) U.S. Cl. .............. 210/651; 210/645; 210/321.75; 210/321.77; 210/321.86
(58) Field of Classification Search ............... 210/651, 210/321.75, 645, 321.77, 321.86, 500.29, 210/500.41
See application file for complete search history.

(56) References Cited

U.S. PATENT DOCUMENTS

| 4,261,834 A | 4/1981 | Dewinter ............... 210/651 |
| 4,618,533 A | 10/1986 | Steuck ................ 428/315.7 |
| 4,629,563 A | 12/1986 | Wrasidlo .............. 210/500.34 |
| 4,761,230 A | 8/1988 | Pacheco et al. ........ 210/321.84 |
| 4,778,601 A | 10/1988 | Lopatin et al. ........ 210/500.27 |
| 4,828,772 A | 5/1989 | Lopatin ............... 264/45.9 |
| 4,874,567 A | 10/1989 | Lopatin et al. ......... 264/45.1 |
| 4,933,081 A | 6/1990 | Sasaki et al. ............ 210/490 |
| 4,944,879 A | 7/1990 | Steuck ................ 21/500.27 |
| 4,976,859 A | 12/1990 | Wechs .................. 21/999.9 |
| 4,983,288 A | 1/1991 | Karbachsch et al. ... 210/321.87 |
| 5,017,292 A * | 5/1991 | DiLeo et al. ............ 210/645 |
| 5,096,582 A | 3/1992 | Lombardi et al. ........ 21/321.6 |
| 5,096,637 A | 3/1992 | DiLeo et al. ............ 264/45.1 |
| 5,147,542 A | 9/1992 | Proulx ................ 21/321.75 |
| 5,171,445 A | 12/1992 | Zepf ................. 210/500.27 |

(Continued)

FOREIGN PATENT DOCUMENTS

| EP | 0083489 | 7/1983 |
| EP | 0364173 | 4/1990 |

OTHER PUBLICATIONS

P. Roberts, "Efficient Removal of Viruses by a Novel Polyvinylidene Fluoride Membrane Filter", J. Virological Methods, vol. 65, pp. 27-31 (1997).

(Continued)

*Primary Examiner*—Ana Fortuna
(74) *Attorney, Agent, or Firm*—Nields & Lemack

(57) ABSTRACT

The present invention provides a high-resolution membrane-based method for removing a virus from a manufactured protein-containing solution, the method being particularly characterized by its capacity to be performed quickly (i.e., as measured by flux) and efficiently (i.e., as measured by log reduction value, LRV). Towards such results, the present invention employs a plurality (i.e., greater than 2) of interfacially-contiguous asymmetric ultrafiltration membranes, the foremost of which is oriented with its "tight side" facing downstream. The present invention also provides a filtration capsule, useful in the conduct of the method, comprising a pleated tube formed of three interfacially-contiguous asymmetric ultrafiltration membranes.

4 Claims, 4 Drawing Sheets

U.S. PATENT DOCUMENTS

| | | | |
|---|---|---|---|
| 5,176,828 A | 1/1993 | Proulx | 21/341 |
| 5,256,294 A | 10/1993 | van Reis | 21/637 |
| 5,444,097 A | 8/1995 | Tkacik | 521/61 |
| 5,456,843 A | 10/1995 | Koenhen | 21/651 |
| 5,522,991 A | 6/1996 | Tuccelli et al. | 210/490 |
| 5,525,144 A | 6/1996 | Gollan | 96/8 |
| 5,599,447 A | 2/1997 | Pearl et al. | 210/321.75 |
| 5,603,900 A | 2/1997 | Clark et al. | 422/101 |
| 5,725,763 A | 3/1998 | Bonhomme et al. | 210/188 |
| 5,736,044 A | 4/1998 | Proulx et al. | 210/488 |
| 5,736,051 A | 4/1998 | Degen et al. | 210/650 |
| 5,788,862 A | 8/1998 | Degen et al. | 210/651 |
| 5,834,107 A | 11/1998 | Wang et al. | 428/310.5 |
| 5,837,365 A | 11/1998 | Chung | 428/318.8 |
| 5,846,422 A | 12/1998 | Ditter et al. | 210/500.41 |
| 5,869,174 A | 2/1999 | Wang | 428/315.9 |
| 5,886,059 A | 3/1999 | Wang | 521/64 |
| 5,906,742 A | 5/1999 | Wang et al. | 210/500.41 |
| 5,928,774 A | 7/1999 | Wang et al. | 428/310.5 |
| 5,928,792 A | 7/1999 | Moya | 428/422 |
| 5,958,989 A | 9/1999 | Wang et al. | 521/64 |
| 5,979,670 A | 11/1999 | Ditter et al. | 210/489 |
| 6,045,899 A | 4/2000 | Wang et al. | 428/315.7 |
| 6,054,051 A | 4/2000 | van Reis | 210/641 |
| 6,074,869 A * | 6/2000 | Pall et al. | 435/286.5 |
| 6,365,395 B1 * | 4/2002 | Antoniou | 435/239 |
| 6,479,273 B1 | 11/2002 | Bogedain et al. | 435/239 |
| 6,565,749 B1 * | 5/2003 | Hou et al. | 210/500.38 |

OTHER PUBLICATIONS

"Ultipor (R) VF Grades DV50 and DVD Virus Removal Filter Cartridges", Pall Corporation Promotional Literature, downloaded from www.pall.com on Oct. 17, 2002.

Journal of Membrane Science 120 (1969) p. 149-159; "Terminology For Membranes and Membrane Processes" W.J. Koros et al.

Filtration in the Biopharmaceutical Industry, Marcel Dekker, Inc. (1988) - Chapter 20.

* cited by examiner

HIGH-RESOLUTION VIRUS REMOVAL METHODOLOGY AND FILTRATION CAPSULE USEFUL THEREFOR

This is a continuation-in-part of U.S. patent application Ser. No. 09/662,410, filed 14 Sep. 2000, now abandoned which claims the benefit of U.S. Prov'l Pat. App. Ser. No. 60/153,830, filed 14 Sep. 1999.

FIELD

The present invention is directed to a method of high-flux, high-resolution removal of a virus from a protein-containing bio-organic fluid, and to a membrane-based filtration capsule useful therefor.

BACKGROUND

Virus removal from liquid streams, particularly process streams in the biotech and pharmaceutical industry, has been practiced for some time. High viral clearance, high product flux, complete protein passage and simplicity of operation are the goals of the operator, yet the prior art does not provide a solution that satisfies all of these goals. Since high viral clearance is always needed, it is the other process goals that have suffered. Meeting these other goals would substantially lower processing cost.

The prior art provides several membrane types and filtration modes for viral clearance. For a general discussion concerning the state of prior art, see Chapter 20 of *Filtration in the Biopharmaceutical Industry*, Marcel Dekker, Inc. (1988). Chapter 20 is entitled "Filtration and the Removal of Viruses from Biopharmaceuticals."

One of the products discussed in Filtration was the Viresolve™ product line produced by Millipore Corporation. This is a system that used a composite ultrafiltration membrane in a tight side-up-stream (TSUS) orientation in a tangential flow filtration (TFF) device.

U.S. Pat. No. 5,017,292 discloses technology used to produce the Viresolve product. It provides a composite membrane comprising a porous membrane substrate, a tight side (the surface having smaller diameter pores) having ultrafiltration separation properties and an intermediate porous zone between the substrate and the skin which intermediate zone has an average pore size smaller than that of the substrate. The intermediate zone is free of macrovoids that may break the skin. The composite membrane is capable of a log reduction value (LRV) of at least 3 (99.9% removal) of virus particles (collectively "virus") selectively from solution. A limitation of this system is that in order to achieve adequate protein solution flux, a complex pumping system is needed to operate effectively in a TFF mode. This needed complexity results in a substantial filtration cost.

While more conventional virus removal applications are available from several manufacturers, they also cannot attain all the goals set forth above. Indeed, they either use conventional ultrafiltration membranes in single layer TSUS orientation in a TFF device or a hollow fiber ultrafiltration TFF device. They similarly lack the simplicity of use and result in a high filtration cost.

Normal flow filtration (NFF) devices, also known as dead—ended filtration devices, are currently available for use in removing viruses from process streams. Indeed, Pall Corp. of East Hills, N.Y. manufactures a dead-ended virus removal membrane under the Ultipore® DV50 brand (hereinafter the "DV50") and DV20 brand (hereinafter the "DV20").

The DV50 consists of three-layers of an isotropic, skinless, porous polyvinylidene fluoride ("PVDF") membrane. While this product has the desired virus removal capabilities and simplicity of use for large virus removal, the isotropic structure of the membranes employed limits its permeability. A low permeability (water permeability of 2 Imh/psi) increases the costs of filtration. This product also does not meet all the goals set forth above.

The DV20 is a similar product, but designed for small virus removal. It has a permeability of 0.6 Imh/psi with IgG.

U.S. Pat. No. 5,736,051 discloses a PVDF membrane and method for removing viruses from solutions. More particularly, it provides an isotropic, skinless, porous PVDF membrane. We believe this is the membrane used in the DV50 and DV20.

U.S. Pat. No. 5,788,862 discloses a supported ultrafiltration membrane with a coated skin. In the patent, the membrane is described as having been used in a 2-layer configuration in NFF mode with a coated skin to filter viruses from protein streams. While satisfactory levels of virus removal were achieved, the protein passage and flux were very low: maximum disclosed flux with IgG was 0.6 Imh/psi and max IgG passage was only 84%.

In addition to the prior art providing multi-layered virus removal membranes, the prior art also provides multi-layered ultrafiltration membranes with at least one membrane being oriented TSDS. U.S. Pat. No. 4,261,834 provides two anisotropic ultrafiltration membranes positioned in series with at least one membrane juxtaposed with at least one other membrane so that substantially all the skin surface of one membrane is in intimate contact with substantially all of the skin surface of the other membrane. This invention, however, was directed to mask pinhole defects for ultrafiltration membranes used to remove proteins (pyrogens) from aqueous streams in a tangential flow filtration (TFF) system.

In light of the above, there is a clear need for filtration materials and devices that remove viruses at high log reduction values (LRV), having essentially complete passage of the protein product and operating at high flux. Furthermore, there is a need that such materials and devices should be easy to operate, preferably in NFF mode.

SUMMARY

In response to the aforementioned needs, the present invention provides a high-resolution membrane-based method for removing a virus from a manufactured protein-containing solution, the method being particularly characterized by its capacity to be performed quickly (i.e., as measure by flux) and efficiently (i.e., as measured by log reduction value, LRV). In the accomplishment of such results, the present invention employs a plurality (i.e., at least 2) of interfacially-contiguous asymmetric ultrafiltration membranes, the foremost of which is oriented with its "tight side" facing downstream. Typically, at least two of the asymmetric ultrafiltration membranes are oriented with their "tight side" facing downstream.

Conduct of the methodology involves flowing a manufactured protein-containing solution through a filtration device containing the asymmetric ultrafiltration membranes under conditions sufficient to effect passage of said protein through said asymmetric membranes, and whereby any of a specifically-targeted virus contaminating said protein-containing solution, being substantially prevented from passing through said asymmetric membranes, is substantially removed therefrom.

A "manufactured protein-containing solution" as used herein is a term of specific definition. In contrast to a solution having naturally-occurring protein content (e.g., water having naturally-occurring microbial content), the protein content in a "manufactured" solution will be enriched, as a result of human intervention and possible conduct of other solution refinement processes, such that the predominant solute in said solution is said protein.

In respect of the asymmetric membranes, several criteria need to be present to perform the inventive methodology. First, at least two asymmetric membranes must be employed. Second, each must be substantially hydrophilic. Third, at least two of the asymmetric membranes must be capable of substantially preventing the passage therethrough of the targeted virus, whilst substantially permitting the passage therethrough of the bio-manufactured protein. Fourth, at least two of the asymmetric membranes must each have a tight-side and an open-side, the average surface pore size of said tight-side being less than the average surface pore size of said open-side. And finally, the foremost asymmetric membrane must be oriented such that fluid introduced into the aforementioned filtration device commences passage through this asymmetric membrane through its open-side.

Aside from, but relevant to, the virus removal methodology, the present invention also provides a filtration capsule comprising a pleated tube formed of three interfacially-contiguous asymmetric ultrafiltration membranes. Although perhaps having applicability elsewhere, this product configuration has been found quite effective in the conduct of the inventive virus removal methodology, in respect of its durability, reliability, cost, and ease of use and replacement.

In light of the above, it is a principal objective of the present invention to provide a methodology for removing at a high resolution a virus from a manufactured protein-containing solution, and particularly, one capable of being performed effectively at a log reduction value of greater than 6, at a flux of either approximately 5–20 lmh/psi for a comparatively large virus (e.g., murine leukemia virus) or approximately 2–4 lmh/psi from a comparatively smaller virus (e.g., parvo virus).

It is another principal objective of the present invention to provide a filtration capsule useful for conducting said virus removal methodology.

It is another object of the present invention to provide a large virus removal methodology with high process fluxes, i.e., greater than 5 lmh/psi, preferably greater than 10 lmh/psi, and even more preferably, greater than 20 lmh/psi.

It is another object of the present invention to provide a small virus removal methodology with high process fluxes, i.e., greater than 2 lmh/psi, preferably greater than 3 lmh/psi, and even more preferably, greater than 4 lmh/psi.

It is another object of the present invention to provides a device that includes a multi-layered membrane filtration material suitable for filtering viruses, the material comprising at least two asymmetric void-free membrane layers, of which the upstream layer's "tightest" side is oriented downstream.

It is another object of the present invention to provide a device for removing a virus from a solution, the device comprising a housing suitable for containing a filtration material and further characterized by an inlet for receiving fluid to be filtered and an outlet for removing filtrate, the filtration material including at least two layers of tight side, asymmetric void-free membranes, the upstream layer oriented such that its "tightest" side faces downstream.

It is another objective of the present invention to provide a membrane suitable for use in a multi-layered, virus removal device, the membrane comprising a "tight side", a porous support, and a pore size range suitable for ultrafiltration, the membrane further characterized by having an asymmetric structure substantially free of unwanted, so-called "macrovoid" artifacts (i.e., surface-to-surface cracks, fissures, openings, and like structural detriments to good retention) and having surfaces that upon exposure to a protein-containing solution, exhibit low protein binding (i.e., low protein affinity).

It is another objective of the present invention to provide a virus removal device comprising filtration material and characterized by having a Vmax greater than 10 ml/cm$^2$ (but preferably, at least 18 ml/cm$^2$), a log reduction value (LRV) greater than 6, and a protein passage greater than 98%, when challenged with a suspension containing at least 10$^7$ pfu/ml of bacteriophage $\phi$6 (size 78 nm) and monoclonal IgG at a concentration 2.5 mg/ml, at volumes up to 50 ml/cm$^2$ of tested filter.

It is another objective of the present invention to provide a process for producing a polymeric ultrafiltration membrane suitable for virus removal, the process comprising dissolving a polymeric material in a suitable solvent, filtering and degassing the casting solution, heating the casting solution to its cloud point, casting the solution onto a belt passing over a casting drum submerged in water, the solution having a short residence time on the drum; using a knife to set the cast thickness, exposing the cast film to dry air, immersing the cast film in the water bath, extracting the membrane from the water bath, and hydrophilizing the membrane in a monomer solution.

It is another objective of the present invention to provide the aforementioned virus removal device, wherein the layers of the filtration material are substantially similar, and are comprised of polyethersulfone or regenerated cellulose.

It is another objective of the present invention to provide the aforementioned virus removal device, wherein the filtration material is a composite membrane.

It is another objective of the present invention to provide the aforementioned virus removal device, wherein the upstream layer of the filtration material is a high integrity ultrafiltration membrane, or more preferably, wherein all membrane layers of the filtration material are high integrity ultrafiltration membranes.

It is another objective of the present invention to provide the aforementioned virus removal device, wherein the layer of membrane positioned immediately downstream of the first layer is also oriented with its "tight side" facing downstream, and more preferably, wherein the device has three layers of filtration material and this downstream (third) layer is also oriented with its "tight side" facing downstream.

It is another objective of the present invention to provide the aforementioned virus removal device, wherein the housing used therefor is suitable for receipt of liquid from a syringe, or is adapted for dead-ended filtration, or has a capsule configuration, or is adapted to receive the filtration material in disk form and may be reused.

Other objectives of this invention will become apparent from the following detailed description of the presently preferred embodiments of the invention, taken in conjunction with the accompanying drawings.

Definitions

Figure 1:
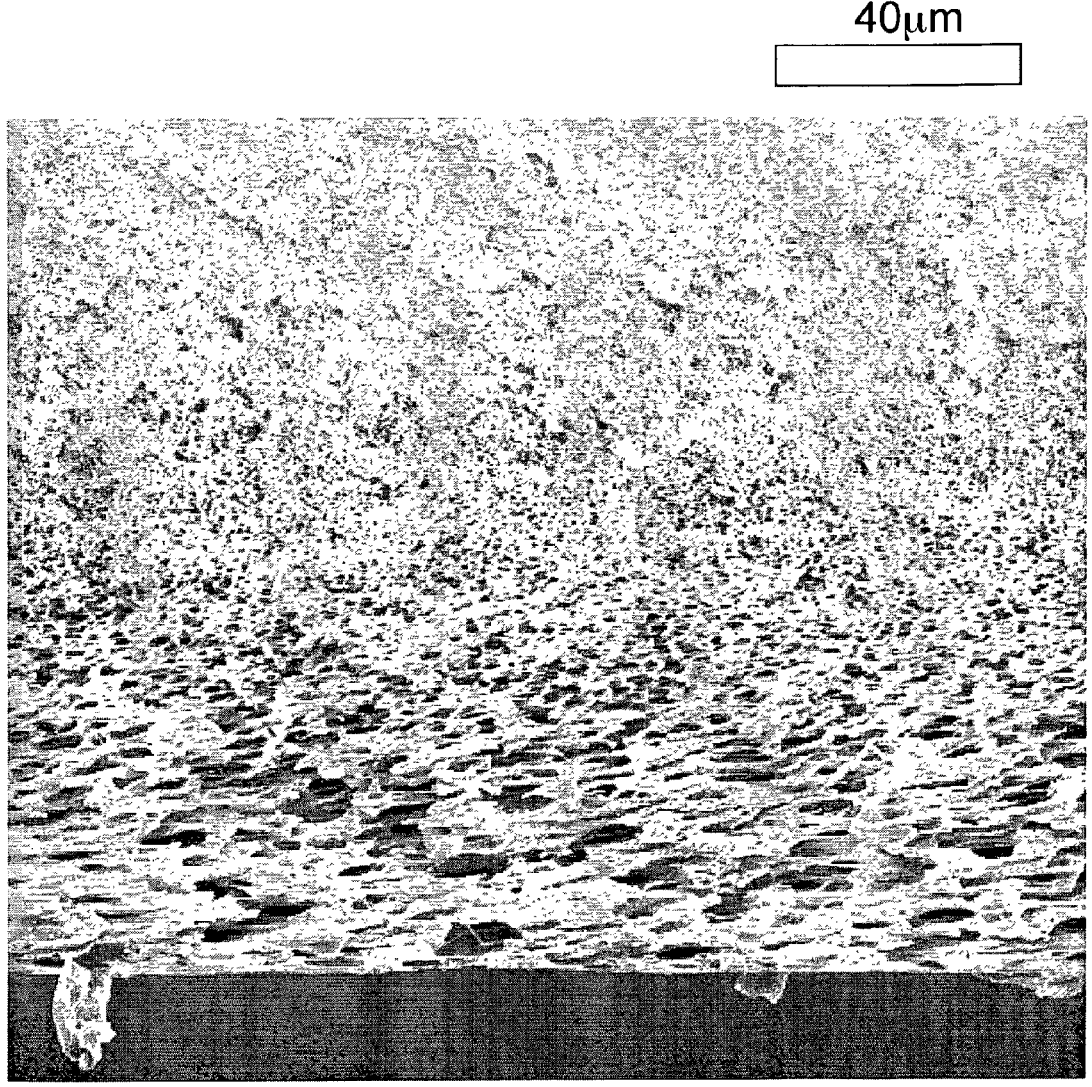
FIG. 1 provides a scanning electron micrograph of a high-integrity asymmetric ultrafiltration membrane, which is further described in Example 1 infra.

To the extent used herein, and solely for the purpose of construing the scope of the present invention, the following selected terms shall be defined as follows.

A "high integrity ultrafiltration membrane" shall be defined as an asymmetric ultrafiltration membrane substantially free of macrovoids and capable of achieving a minimal automated ramp bubble point (APB) of 87 psi when tested in TSDS orientation.

A "multi-layered membrane filtration material" shall be defined to include membranes with a minimal distance between them, such as membranes with a measurable distance between them, and membranes incorporated into separate housings. In certain embodiments of the present invention, the layers of a multi-layered membrane filtration material are stacked one on top of the other and contained in the same housing.

A "pre-filter layer" shall be defined as any material used to filter matter from the fluid process stream of interest with the objective of increasing the throughput of the filter device. In certain embodiments of the present invention, such pre-filter layer will have a substantially lower viral retention than the foremost upstream layer of a multi-layered ultrafiltration material.

Although these and other terms are expressly defined herein, and should be construed accordingly, further guidance on the generally accepted meaning of terms used but not expressly defined herein and/or otherwise commonly used in the field of membranology can be found, for example, in W. J. Koros, et al., "Terminology for Membranes and Membrane Processes", IUPAC Publication (1996).

DETAILED DESCRIPTION

The present invention provides a virus removal methodology suitable for conducting at high-flux fluid separation of a virus from a protein.

The methodology commences by obtaining, preparing, assembling, or otherwise providing for use a filtration device that, in its fundamental structure, comprises a housing having a fluid inlet and a filtrate outlet, and that contains at least two asymmetric membranes. The asymmetric membranes—i.e., all asymmetric membranes employed including the minimum two—should each be substantially hydrophilic. At least two of the asymmetric membranes should each be capable of substantially preventing the passage therethrough of said virus and substantially permitting the passage therethrough of said protein. These two should also each have a "tight-side" and an "open-side", wherein the average surface pore size of said tight-side is less than the average surface pore size of said open-side. The foremost asymmetric membrane should be positioned within the filtration device's housing such that when fluid is introduced into the housing through the fluid inlet, the fluid will impinge first upon and commences passage through this asymmetric membrane through its open-side. Whether an asymmetric membrane is "foremost" is determined with respect to process flow, i.e., the first asymmetric membrane contacted by fluid introduced into the filtration device.

Prior or after provision of the filtration device, a manufactured protein-containing solution is obtained, prepared, composed, or otherwise provided for use. Although the predominant solute in the manufacture protein-containing solution is the target protein of interest, incidents of its manufacture and composition render it prone to viral contamination. Additional and more particular details of the manufactured protein-containing solution are set forth further below.

Provided with both the filtration device and the manufactured protein-containing solution, the methodology continues and concludes with the flowing of said manufactured protein-containing solution through said filtration device under conditions sufficient to effect passage of said protein through each of said asymmetric membranes and out of said housing through said filtrate outlet, such that any of a targeted virus contaminating said protein-containing solution—being substantially prevented from passage through said asymmetric membranes—is substantially removed therefrom.

In the performance of the viral removal methodology, there are no particular limits on the construction, scale, or composition of the filtration device other than that it comprises a housing that has a fluid inlet and a filtrate outlet. Both "normal flow"- and "tangential flow"-type filtration devices are envisaged. Examples of the such devices are well represented in the patent literature.

For example, for "normal flow"-type filter configurations mention can be made of U.S. Pat. No. 5,725,763, issued to L. Bonhomme et al. on Mar. 10, 1998; U.S. Pat. No. 5,603,900, issued to P. Clark et al. on Feb. 18, 1997; Eur. Pat. App. Pub. No. 0 364 173 by R. W. Philpott, dated Apr. 18, 1990; Eur. Pat. App. Pub. No. 0 083 489 by W. J. Wrasidlo et al. dated Jul. 13, 1983; and U.S. Pat. No. 4,983,288, issued to Karbashschet al., on Jan. 8, 1991. "Normal flow"-type filter configurations are also commercially available, for example, from Millipore Corporation (Bedford, Mass. 01730) under the tradenames "Millex", "Opticap", "Sterivex", "Steripak", "Millipak", and "Sterivak".

For "tangential flow"-type filter configurations mention can be made of U.S. Pat. No. 4,261,834, issued to D. M. deWinter on Apr. 14, 1981; U.S. Pat. No. 6,054,051, issued to R. D. van Reis on Apr. 25, 2000; 4,761,230, issued to J. F. Pacheco et al. on Aug. 2, 1988; 5,096,582, issued to A. A. Lombardi et al. on Mar. 17, 1992; 5,256,294, issued to R. D. van Reis on Oct. 26, 1993; and U.S. Pat. No. 5,525,144, issued to A. Z. Gollan on Jun. 11, 1996. "Tangential flow"-type filter configurations are also available commercially: e.g., "Pellicon XL" and "Pellicon 2" TFF cartridges (available from Millipore Corporation of Bedford, Mass. 01730); and "Centramate", "Centrasette", "Maximate" and "Maximate-Ext" TFF cartridges (available from Pall Corporation of East Hills, N.Y. 11548).

Although not all embodiments described in the patents above will be suitable for use in the inventive methodology, the determination of which would be suitable, and/or any engineering needed to render such suitable, is felt to be within the skill in the art.

Although the practice of the inventive methodology is not limited to any particular structural configuration for the filtration device housing the asymmetric ultrafiltration membranes, one particular filter capsule configuration has been found to provide desirable results in performing the inventive methodology. It may also provide good results for other viral removal applications (i.e., the removal of viruses from non-biopharmaceutical protein-containing solutions, such as water, opthalmic saline solutions, and beverages).

In general, it has been found that by incorporation of multiple asymmetric ultrafiltration membranes, arranged in a pleated configuration with the membranes in "tight side down stream" orientation, the resulting filter capsule will have good viral retention capabilities, yet maintain good flux. Although these may not be as high without using all the teaching underlying the inventive methodology, such high degree of accomplishment (particularly with respect to viral retention) is not always required in all circumstances. For example, for certain non-pharmaceutical purification applications, log viral reduction values need not approach a value greater than 2.

As to its particular structure, the filtration capsule comprises a tubular housing and a pleated filtration tube substantially co-axially enclosed within said housing. A representative example of such filtration capsule is presented—for purposes of illustration only—in FIG. 2B.

The tubular housing of the filtration capsule is constructed to contain and channel a fluid process stream conducted therethrough—and accordingly, as shown in FIG. 2—is provided with a fluid inlet 20 and a filtrate outlet 30. The fluid process stream u, upstream of the pleated filtration tube, is introduced into the filtration capsule 10 through the fluid inlet 20. Downstream of the pleated filtration tube, the fluid process stream d is released from the filtration capsule 10 through filtrate outlet 30.

The materials used for the tubular housing will depend largely on its intended application. Injection-moldable thermoplastic materials are the most likely candidates. However, the use of metals, glass, and ceramics are also contemplated. If sought for use in viral clearance of biopharmaceutical protein products, the material selected should be compatible with the fluids (e.g., solvents) and environmental parameters (e.g., temperature and pressure) involved therein, and should have low protein-binding characteristics. A preferred material in this regard is polypropylene.

Because filtration devices, in general, often need to satisfy several structural and functional criteria in the course of most filtration protocols, it is unlikely that its overall construction, including its housing and any internal components, will be simple. Although a single continuous and unitary structure is possible, in all likelihood the tubular housing will comprise several cooperating assembled parts. See e.g., FIG. 2B, which illustrates a tubular housing that comprises an upper shell 12 and an end cap 14.

The pleated filter tube is positioned within the tubular housing such that it will divide, in operation, the fluid process stream that flows between the fluid inlet 20 and the filtrate outlet 30. The pleated filter tube 50 is composed of three interfacially-abutting asymmetric membranes. Each of the asymmetric membranes are identical in the following respects. First, they are each substantially hydrophilic. Second, they are each capable of substantially preventing the passage therethrough of viruses. Third, they are each provided with a tight-side and an open-side, wherein the average pore size of said tight-side is less than the average pore size of said open-side. And fourth, they are all oriented such that fluid introduced into said housing through the fluid inlet commences passage through each respective asymmetric membrane through its open-side.

The pleats of the filter tube can be configured in a corrugated shape or spirally positioned and can have a loop-shaped cross section or a folded cross-section, such as a W-shaped cross-section. As used herein, the term "pleat" or "pleated" is intended to include all such cross-sectional shapes. Relative to occupied volume, the pleated structure presents to an incoming fluid process flow more surface area than that which would be presented by use of flat sheet. This is of particular advantage in consideration of the desire to maximize flux, especially when dealing with high-resolution viral clearance protocols.

Figure 2A:
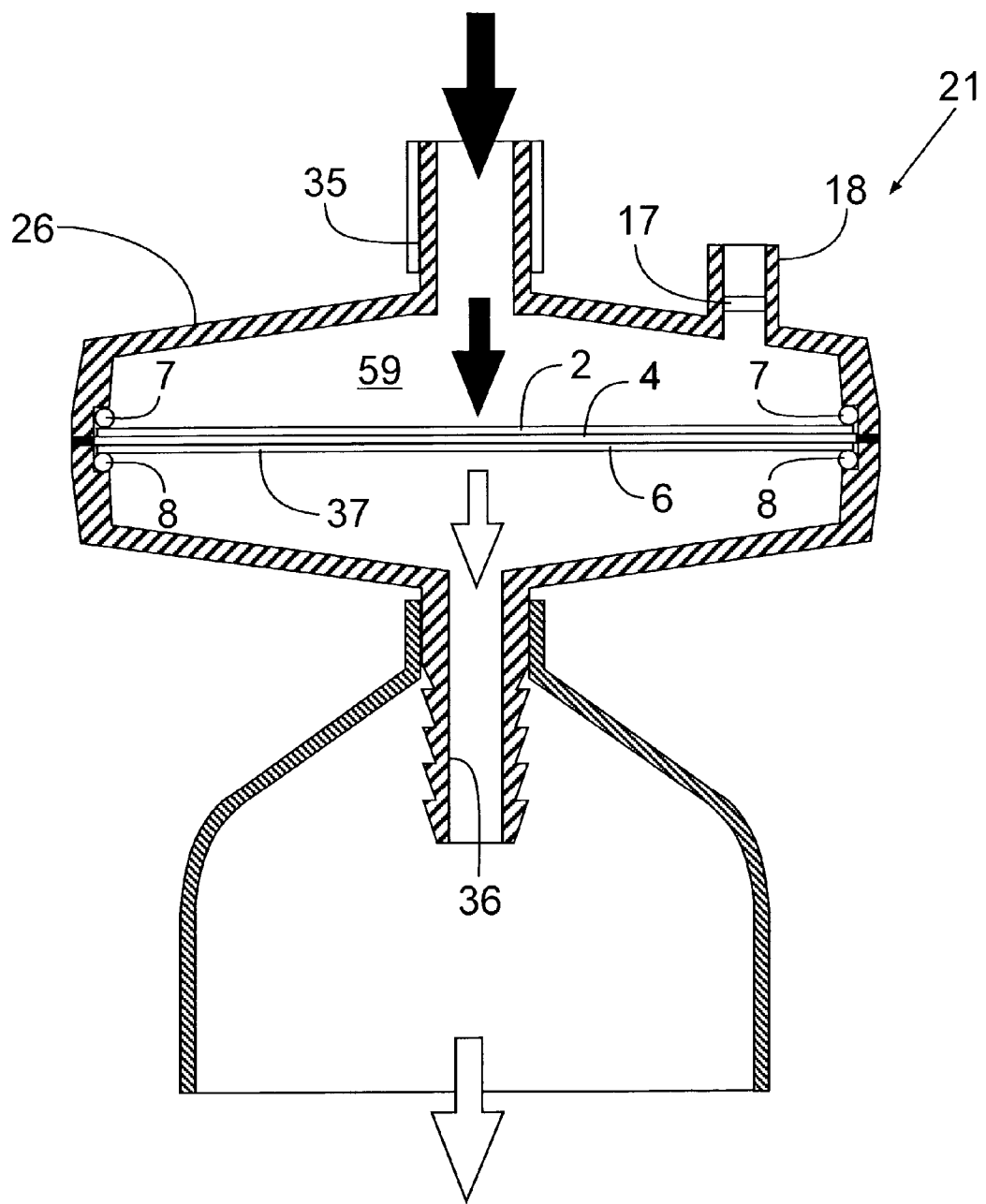
FIG. 2A provides a schematic cross-sectional view of a filtration device 21 useful in the conduct of the inventive protein-virus separation methodology, according to an embodiment thereof.
Figure 2B:
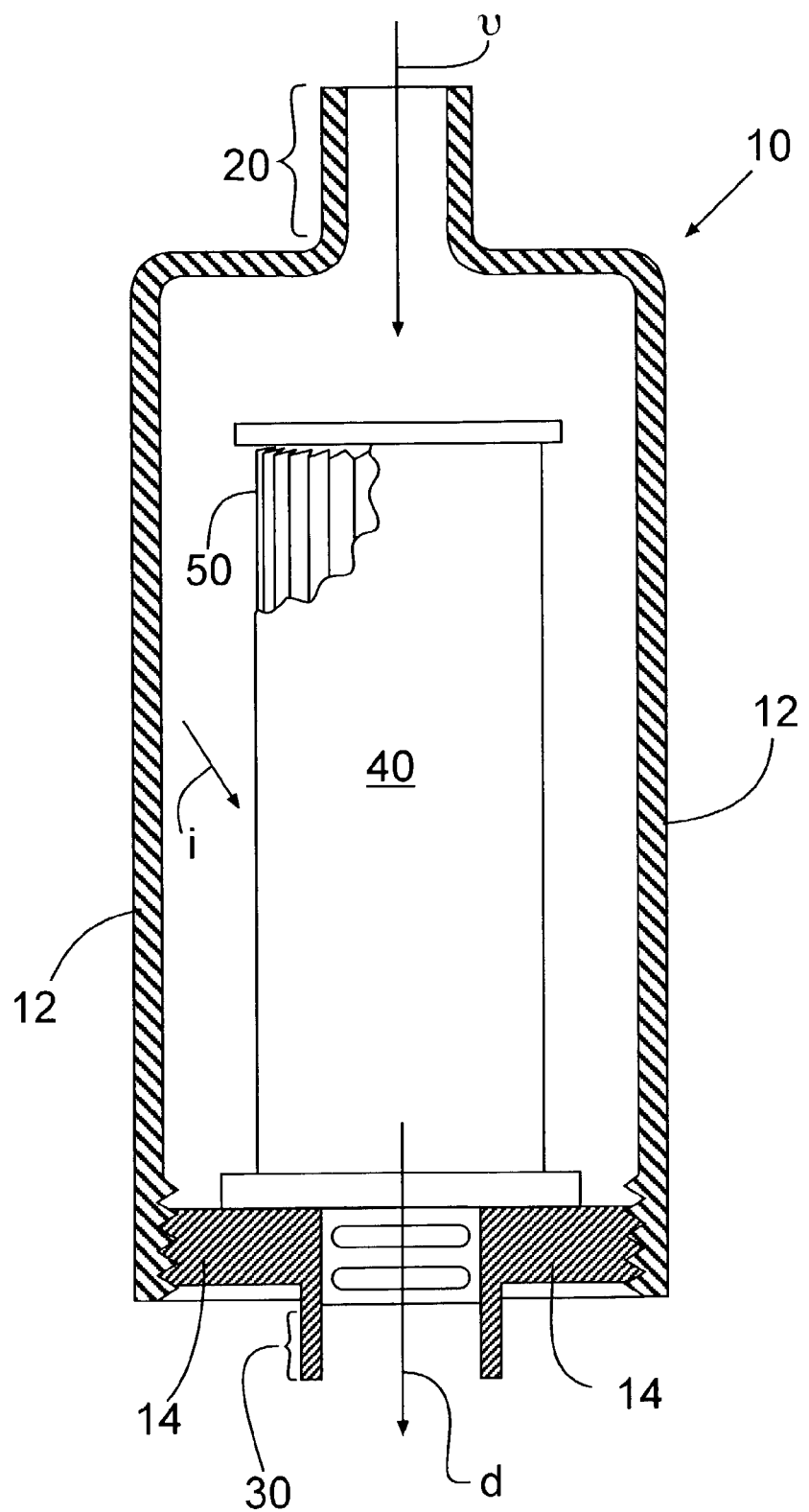
FIG. 2B provides a schematic cross-sectional view of a filtration capsule 10 according to a product embodiment of the present invention, said capsule 10 being useful for performing said protein-virus separation methodology.

The pleated filter tube 50 is shown (through the "cutaway") in FIG. 2B packaged within a replaceable cartridge 40. While it is possible, at least conceptually, to place pleated filter tube 50 within the filter capsule 10 without the agency of a cartridge, replaceable or otherwise, in practice, commercial and environmental advantages are realized by allowing the possibility of easily replacing a spent pleated filter tube 50, without having to undergo burdensome and/or cumbersome dismantling procedures, and/or requiring disposal of an entire filter capsule 10. In the embodiment shown in FIG. 2B, replacement is performed by unscrewing end cap 14 from upper shell 12, unplugging a spent filter cartridge from the filtrate outlet 30 to which it is frictionally mated, plugging therein a fresh cartridge, and screwing the cap 14 back on.

The single tubular pleated sheet 12 is maintained in its relatively fixed tubular conformation within the filter capsule 10 by use of the external and internal supports that together form the replaceable cartridge 40. These supports—the external one being the only one visible in FIG. 2—are made of rigid material and provided with uniformly dispersed holes (not shown) to allow the inward flow i of fluid from regions peripheral to the pleated filter tube 50, through the membranes thereof into tube 50's core, and then ultimately out of filter capsule 10.

For further details regarding the construction and functions of a replaceable filter cartridge, reference can be made to U.S. Pat. No. 5,736,044, issued to S. Proulx et al. on Apr. 7, 1998. Among other subject matter, the patent describes a composite filter cartridge that includes both sheet membranes and depth filters. Aspects of such composite filter can be imported into the construction of the present filter capsule 10, without departing from the spirit and scope of the invention as defined herein.

In respect of another filter housing embodiment useful in the practice of the inventive viral clearance methodology, attention is now directed to FIG. 2A. Therein, there is illustrated schematically a vented liquid filtration system 21 employing a three-layer stack of asymmetric ultrafiltration membranes 37. The vented liquid filtration system 21 comprises a filtration housing 26 and the membranes 37. As shown, the filtration housing 26 defines a filtration passage having a fluid inlet 35 and a filtration outlet 36 and—as schematically represented by the use of the larger graphical arrows—is capable of containing a manufactured protein-containing liquid process stream flowing therethrough. The asymmetric membranes 37 are positioned in the filtration passage between the filtration inlet 35 and the filtration outlet 36 such that the protein-containing liquid process stream must pass through the membranes 37 as its flows through the filtration passage. In accordance with the inventive method, each of the asymmetric membranes are oriented such that fluid introduced into said system 21 through the fluid inlet 35 encounters the membrane at its "open-side".

As shown in FIG. 2A, the three asymmetric membranes 37 are adjacent and contiguous. Space between the membranes should in practice be avoided, otherwise undesired inter-membrane lateral flow may occur and comprise retention. Adhesives should generally not be employed to establish interfacial contiguity as such would tend to fill the pores of the membrane. If felt appropriate, one can resort to the well-known use of paired external rigid screens and/or peripheral frames. Such structural components can be made integral and continuous with the filtration system 21's housing 26.

During the filtration of a liquid process stream in the liquid filter assembly 21, gas can sometimes accumulate in the area between the assembly's filtration inlet 35 and its selectively-permeable filtration element 37. (See, area 59) Accordingly, a gas vent 18 is provided within this area to vent or otherwise release accumulated gas, which can be potentially problematic. A barrier membrane 17 may be employed within vent 18 to prevent the release of the process fluid, while still allowing the passage therethrough of the accumulated gas.

The asymmetric membranes may either be inserted into the housing in a replaceable disk-like cartridge—much in the same way as the earlier described embodiment—or it may be permanently installed by sealing them into the housing round their periphery by means well known in the art.

To accommodate a syringe, the entry port may also be provided with a so-called "luer lock", the structure and assemblage of which is also well known in the art.

The asymmetric membranes used in the present invention are essentially unitary, single- or multi-layer, sheet-like structures. Asymmetry is determine by the average pore size of the membrane's front and back surfaces, i.e., it's so-called "open side" and "tight side", respectively. The average pore size of the asymmetric membrane's "tight side" is less than the average pore size of the membrane's "open-side". The intermediate bulk of the membrane between these sides—whether constituted of a unitary composite of several layers or a single continuous and homogenous layer—will typically have a porous structure that gradually "tightens" up in the transition from the "open side" to the "tight side" (i.e., the fluid-accessible channels and pathways created thereby become on average narrower). This stands in contrast to so-called "skinned" isotropic membranes which, although possessing surfaces of differing average pore size, do not possess a functionally-significant gradual transition between said surface. The gradual change from the "open side" to the "tight side", as perceived when the sheet is viewed in cross-section, can be linear, sinusoidal, exponential, stepped, or other such predetermined non-random pattern. A highly asymmetric membrane structure, e.g., greater than an approximately 10:1 average pore size ration between "open" and "tight" sides, has been found to yield good results.

In a fundamental sense, any method that can produce a so-called "ultrafiltration" type membrane can be employed. Methods of making such membranes are well documented in the patent literature. See, for example, U.S. Pat. No. 5,928,774, issued to I. Wang et al. on Jul. 27, 1999; U.S. Pat. No. 5,837,365, issued to T. C. Chung on Nov. 17, 1998; U.S. Pat. No. 5,456,843, issued to D. M. Koenhen on Oct. 10, 1995; and U.S. Pat. No. 4,976,859, issued to F. Wechs on Dec. 11, 1990. This brief listing is far from exhaustive. Other patents and technical literature certainly exist.

Asymmetric membranes, such as the cellulose acetate membranes known in the art, are conventionally prepared using a solution casting process. In this process a polymer (such as cellulose acetate, polysulfone, and polyamide resins) is dissolved in a mixture of solvents of diverse volatilities, swelling agents and pore forming substances. The solution is cast into a thin film and the more volatile solvents are allowed to partially evaporate. The film is then immersed in a non-solvent of the polymer to precipitate the polymer and to thereby form the asymmetric structure.

As those skilled in the art are aware, the overall properties for the asymmetric UF membranes of the present invention can be fine-tuned by controlling such parameters as polymer concentration, solvent and non-solvent nature and concentration, relative degree of homogeneity or stability of the casting dope solution, exposure time to a gaseous environment following casting, quenching liquid composition, and system variables such as temperature, casting process, casting knife gap, and the like. Routine experimentation may be required to optimize properties for each particular system.

In order to accomplish the high-resolution flux of the present invention, it is important that the asymmetric ultra-filtration membrane be substantially hydrophilic. In this regard, it will be appreciated that certain membrane manufacturing methodologies employ polymers that are either hydrophobic or have very low surface energy. A hydrophilization process can be performed to render such membranes useful for the present invention.

Suitable processes for rendering membranes hydrophilic are known. For example, U.S. Pat. No 4,944,879, issued to M. J. Steuck on Jul. 31, 1990, describes a membrane surface treatment methodology, wherein a hydrophobic membrane is coated with one or more hydrophilic monomers, and then cross-linked onto the surface of the membrane and its pores, rendering hydrophilic the coated and crosslinked regions of the membrane. U.S. Pat. No. 5,928,792, issued to W. Moya on Jul. 27, 1999, describes another surface treatment methodology, wherein a hydrophilic perfluorocarbon copolymer composition is provided onto a hydrophobic membrane formed from PTFE and other fluorinated resins. U.S. Pat. No. 4,618,533, issued to M. J. Steuck on Oct. 21, 1986, describes directly coating a membrane, throughout its entire surface, with a polymerized cross-linked monomer having the desired hydrophilic surface properties. The monomer is deposited on the surfaces of the porous membrane by graft polymerization and/or by deposition of a cross-linked monomer. This method is used in Example 1, infra.

Individually, the asymmetric membranes are each capable of substantially preventing the passage therethrough of the targeted virus, whilst substantially permitting the passage therethrough of protein. This functionality results principally from the pore size of the membrane (i.e., ultrafiltration-sized pores) and its composition (e.g., hydrophilic and low protein-binding).

While the stated functionality is integral to the practice of the inventive methodology, good or otherwise acceptable the inventive results will not necessarily be obtained simply by using membranes that fall within this basic stated functionality. In other words, just because one employs multiple sequential asymmetric ultrafiltration membranes in a filter cartridge wherein the foremost membrane is in so-called "tight side down stream" (TSDS) orientation, one will not necessarily be able to acceptably separate viruses from a manufactured protein-containing solution at a high flux. At one extreme such cartridge may be able to effect such separation, but only at low flux. At another extreme, the cartridge may pass the solution quite readily (i.e., high-flux), but would allow unacceptably high levels of virus to pass. Other parameters need to be met in order to realize the heretofore incompatible objectives of both good viral retention and high flux. These are described elsewhere herein.

While the present invention is not limited to any specific asymmetric ultrafiltration membrane, or any method for the manufacture therefor, two particular membrane capable of providing notably desirable results should be considered: i.e., the membranes described in U.S. Pat. No. 5,017,292, issued to A. J. DiLeo et al. on May 21, 1991; and U.S. Pat. No. 5,522,991, issued to R. Tuccelli et al. on Jun. 4, 1996.

The composite membrane described in U.S. Pat. No. 5,017,292, in general, comprises a porous membrane substrate, a surface skin having ultrafiltration separation properties and an intermediate porous zone between the substrate and the skin. The intermediate zone has an average pore size smaller than that of the substrate. Also, the intermediate zone is free from unwanted voids (i.e., defects) that break the skin. The thickness of the intermediate zone is larger than a thickness where the intermediate zone becomes collapsed or non-uniform and smaller than that where voids typical of ultrafiltration membranes are formed. In general, the ultrafiltration skin and intermediate zone are characterized by small pores which provide a molecular weight "cut-off" of between about $5 \times 10^2$ and $5 \times 10^6$ daltons.

The composite membrane is formed by casting a polymer solution containing between about 10 and 21% polymer onto a microporous membrane. The cast polymer solution then is converted to a porous ultrafiltration skin and a porous intermediate zone by immersing the coated membrane into a liquid which is miscible with the solvent component of the polymer solution.

The substrate component of the composite membrane is formed of a synthetic material having a substantially continuous matrix containing pores or channels of a mean pore size between about 0.05 and 10 micrometers. The substrate can be a microporous membrane, a nonwoven substrate, a woven substrate, or a porous ceramic. A wide variety of polymeric materials can be utilized as the membrane, woven substrate or nonwoven substrate. Examples of these polymers, include: polyolefins, such as low density polyethylene, high density polyethylene, and polypropylene; vinyl polymers such as polyvinyl chloride and polystyrene; acrylic polymers such as polymethylmethacrylate; oxide polymers such as polyphenyl oxide; fluoro polymers, such as polytetrafluoroethylene and polyvinylidene chloride; and condensation polymers, such as polyethylene terephthalate, nylons, polycarbonates and polysulfones.

The skin and intermediate zones of the composite membrane are made from a polymer solution as describe herein. Exemplary polymer solutions can be produced from all of the polymer suitable for forming the porous substrate as set forth above and including solutions of polyvinylidene difluoride, cellulose esters such as cellulose acetate, polyimides such as polyethermide, polysulfones, such as polyethersulfone and polysulfone, polyacrylonitrile, and the like.

An embodiment of a membrane prepared in the spirit of U.S. Pat. No. 5,017,292 is used in Example 4, infra.

The membrane described in U.S. Pat. No. 5,522,991, in general, a defect-free cellulosic ultrafiltration membrane formed from a microporous polymeric substrate which is resistant to high pH (alkaline) conditions and a cellulose ester or cellulose ultrafiltration layer. The thickness of the ultrafiltration layer is controlled so that it is rendered essentially defect-free. The degree of penetration of the cellulose ester or cellulose into the base resistant microporous polymeric layer is controlled to prevent excessive plugging of the substrate pores thereby to maintain desirable flux characteristics of the cellulosic membrane. The degree of penetration is also controlled to effect a strong bond between the layers, thereby frustrating delamination.

This membrane is formed by passing a base resistant polymeric microporous substrate and a solution of cellulose or a cellulose ester into a nip formed by (a) rubber roller with or without a film thereon and (b) a rotating cylinder. The coating thickness of the ultrafiltration layer (as well as its penetration into the microporous support) is controlled by the pressure at the nip, the physical properties of the roll, solution viscosity, and process speed. Optionally, the cellulose or cellulose ester solution can be applied by other well-known coating methodologies, e.g., knife coating, slot coating, etc. The coated microporous substrate is then contacted with a non-solvent for the cellulose or cellulose ester to effect its precipitation to form the ultrafiltration layer.

The base resistant microporous polymeric membrane has pore sizes between about 0.05 and 10 microns, preferably between about 0.2 and 1.0 microns. Suitable base resistant microporous membrane substrates are formed from a polyolefin such as polyethylene or polypropylene; polysulfone, polyethersulfone, polyarylsulfone, polytetrafluoroethylene, cellulose or the like. Particularly suitable microporous membrane substrates are formed from ultrahigh molecular weight polyethylene (UHMW-PE) such as those disclosed by U.S. Pat. Nos. 4,828,772 and 4,778,601. A particularly suitable microporous polypropylene membrane substrate is disclosed by U.S. Pat. No. 4,874,567. The base resistant microporous polymeric membrane substrate is not degraded when contacted with a base solution utilized to convert cellulose ester to cellulose.

The ultrafiltration layer is formed from a solution of cellulose or a cellulose ester such as cellulose diacetate, cellulose triacetate, cellulose nitrate or mixtures thereof. After being deposited on the microporous membrane substrate the cellulose ester can be converted to cellulose by reaction with an aqueous basic solution such as NaOH, KOH, LiOH at a pH between about 11.8 and 12.2. The cellulose ester solution is formed with a solvent composition such as acetone, N-methyl pyrrolidone (NMP), dimethylacetamide (DMAC), mixtures thereof or the like.

An embodiment of a membrane prepared in accordance with U.S. Pat. No. 5,522,991 is used in Examples 1 and 2, infra.

The filtration medium—i.e., the asymmetric ultrafiltration membranes in combination—can be used in suitable filters, filtration cartridges, and the like. Of course, in view of the excellent removal efficiency of the such filtration medium, as well as its low susceptibility to protein adsorption, the present inventive filtration medium can be used in dead-end filtration applications, as well as in tangential, cross-flow, and dynamic filtration applications. In certain embodiments, protein minimally binds to the surfaces of the filtration material of the present invention. The filtration medium is expected to be especially useful in filter elements, such as filter cartridges, which are known to those of ordinary skill in the art. Preferred filter elements utilizing the filtration medium comprise the filtration medium in sheet form, wherein the layers of membrane are stacked one upon the other and are bonded with a thermoplastic seal inside a housing, such as the Millex™ filter cartridges sold by Millipore Corporation.

The filtration medium can be used in flat sheet form. It can also be used in the aforementioned corrugated (pleated)

form in a filter element so as to provide a large membrane surface area for the volume of the filter element. In this format, a capsule-type housing can be used, such as the housing currently used with the Opticap™ filter sold by Millipore Corporation. The other aspects of the filter element may be of any suitable construction and prepared from any suitable material. The filter element can be constructed using techniques that are well known in the art.

The protein-containing solution treated under the inventive method are those typically extracted from industrially-manufactured cell cultures for the purpose of accessing, for example, the biopharmaceutical activity of said protein. Many of these protein are quite complex in their structure, and are increasingly used in research, diagnostics and therapeutics. Regardless, the exact constituency of the protein-containing solution should not be perceived as limiting unduly the scope of the present invention. Clearly, non-manufactured fluids, such as water (e.g., tap, drinking, reservoir, laboratory, and the like) are not included. However, in biopharmaceutical manufacturing processes, there are a number of points at which a fluid in which protein is present. The present invention does not seek to capture all such fluids. Rather, the inventive methodology is drawn to a "manufactured" protein-containing solution described herein and set forth in the claims. It is "manufactured" in the sense that the protein contained in said solution is present in a form, purity, and/or concentration that does not naturally exist, for example, it occurs in enriched concentration (i.e., a concentration that does not occur naturally or spontaneously without human intervention) or otherwise has detectable genetically-engineered features. Such scope is best understood in consideration of the basic elements of biopharmaceutical manufacture.

The production of biologically-based diagnostic or therapeutic proteins from genetically-engineered (or otherwise manipulated) cells is a comparatively new technology. The secreted product needs to be purified from the cell culture medium. Most mammalian cells require serum which contains a diverse mixture of proteins, many of which are present at high concentrations. Even in serum-free media systems, numerous other proteins are secreted from the cells. For most of the applications the final product has to meet high levels of purity and activity.

The proteins targeted by the present invention (such as antibodies, hormones, and enzymes) are those manufactured by biopharmaceutical processes. While the field is still comparatively new, and thus subject to change, two processes for producing therapeutically-active or otherwise biologically-significant proteins are commonly-employed—though others exist—in the biopharmaceutical arena: i.e., the secretion of monoclonal antibodies from cloned hybridoma cell lines, and the synthesis of proteins using recombinant DNA technologies.

Monoclonal antibodies are produced by fusing single antibody-forming cells to tumor cells grown in culture. The resulting cell is called a hybridoma. Each hybridoma produces relatively large quantities of identical antibody molecules. By allowing the hybridoma to multiply in culture, it is possible to produce a population of cells, each of which produces identical antibody molecules. These antibodies are called "monoclonal antibodies" because they are produced by the identical offspring of a single, cloned antibody producing cell. With the advent of hybridoma technology and other progress in genetic engineering of eucaryotic cells, mammalian or yeast cell lines are becoming the method of choice for producing complex proteins on a large scale.

Recombinant DNA technology involves the integration of a specific DNA fragment into a rapidly replicating genetic element (e.g., a plasmid) so that it can be amplified in bacteria or yeast cells. These cells multiply in culture, each containing the protein-coding plasmid. Translation of the DNA fragment on the plasmid yields the protein-encoded therein.

The monoclonal antibody and recombinant DNA technologies—among other methods of genetic-engineering—are capable of producing a broad range of proteins. Many of such proteins are currently available. Specific examples include, but are not limited to, such proteins as: recombinant methionyl human granulocyte colony-stimulating factor (175 amino acids) having a molecular weight of 18,800 daltons, available from Amgen, Inc., (Thousand Oaks, Calif. 19320) under the tradename "Neupogen" and used to boost white blood cell production and combat infection from chemotherapy, bone marrow transplants and infectious diseases; recombinant erythropoetin (165 amino acids) having a molecular weight of 30,400 daltons, available from Amgen under the tradename "Epogen" and used to stimulate red blood cell production for treatment of anemia; non-glycosylated interferon alfa-2b (165 amino acids) having a molecular weight of 19,271 daltons, available from Biogen, Inc. (Cambridge, Mass. 02142) under the tradename "Intron A", used in the treatment of different types of cancers and viral infections, including hepatitis B and C; recombinant human insulin lispro having a molecular weight of 5808 daltons, such as available from Eli Lily & Co. (Indianapolis, Ind. 46285), under the tradename "Humulin", used in the treatment of diabetes; the recombinant hepatitis B vaccine (a surface antigen produced by *S. cerevisiae*) available from GlaxoSmithKline, plc, (Middlesex, United Kingdom) under the tradename "Engerix-B" used in the treatment of hepatitis; recombinant tissue plaminogen activator (serine protease enzyme, 527 amino acids), such as available from Genentech Inc., (South San Francisco, Calif. 94080) under the tradename "Activase" used in the treatment of heart attacks and blood clots; the recombinant pituitary-derived growth hormone (192 amino acids) having a molecular weight of 22,000 daltons, available from Genentech under the tradename "Protropin" used in the treatment of human growth deficiency; the recombinant pituitary-derived human growth hormone (191 amino acids) having a molecular weight of 22,125 daltons, available from Genentech under the tradename "Nutropin" used in the treatment of human growth deficiency; the recombinant interferon alfa-2a (165 amino acids) having a molecular weight of 19,000 daltons, available from Roche (Basel, Switzerland) under the tradename "Roferon-A", for use in the treatment of hairy cell leukemia and Kaposi's sarcoma; the monoclonal antibody available from Genentech under the tradename "Herceptin" used in the treatment of HER2 positive metastatic breast cancer; the IgG kappa immunoglobulin (composed of two heavy chains of 451 amino acids and two light chains of 213 amino acids) having an approximate molecular weight of about 145,000 daltons, available from Genentech under the tradename "Rituxan" used in the treatment of non-Hodgkin's lymphoma; the glucocerebrosidase enzyme available from Genzyme under the tradename "Cerezyme" used in the treatment of Gaucher's disease; the recombinant form of interleukin available from Chiron Corporation (Emeryville, Calif. 94608) under the tradename "Proleukin" used in the treatment of metastatic renal cell carcinoma.

There is vast amount of publicly-accessible literature that provides—or from which can be surmised—the specific details by which these proteins are produced. These details are not critically important to the practice of the invention methodology claimed herein. Regardless, while subject to variation, fundamentally, synthetic biopharmaceutical processes yielding manufactured protein-containing solutions will all typically share the following generic stages: Preparation, Production, and Refinement.

The preparation stage essentially involves all the steps leading to the production stage, and includes such steps as: preparing a hybridoma or recombinant cell line for use; preparing a mixture of water, the cellular charge, and growth media; and clarification and/or pre-filtration of said mixture.

The production stage—i.e., cell culture—essentially involves growing the cell culture in a vat (or other suitable container) under condition that foster rapid growth and production of protein. Under certain regimens, gasses such as air and carbon dioxide are added and/or removed. All fluids which come in contact with cells in a reactor or fermentation vessel should be sterile and free from any potentially toxic agents or pyrogens. Small-scale cell culturing can be performed in shallow shaker flasks. The cells and nutrient media are combined in the flask and a mechanical or magnetic stirring mechanism circulates the mixture. This circulation is important to prevent the cells from settling to the bottom of the culture vessel due to gravity and to ensure sufficient nutrient transfer to and waste bioproducts from the growing cells.

In the refinement stage, the vat is essentially emptied and the cell culture fluid is subjected to a sequences of purifying and/or concentration processes that remove the waste (e.g., cellular debris, growth media, and the like) from the product (i.e., a purified protein-containing solution). Various separation and purification methodologies are employed at this stage, and include for example, membrane based filtration, chromatography, crystallization, centrifugation, and the like.

It is within the refinement stage wherein the inventive methodology is employed, together possibly with other purification processes. Typically, as essentially a so-called "ultrafiltration" process, the inventive methodology is best conducted subsequent to removal of larger undesired components of the manufactured protein-containing solution through for example, a series of microfiltration processes—e.g., microporous tangential flow filtration processes designed to clarify, prefilter, and/or concentrate the manufactured protein-containing solution. Several devices are already available for conducting such pre-filtration processes. See e.g., U.S. Pat. No. 5,147,542, issued to A. Proulx on Sep. 15, 1992; U.S. Pat. No. 5,176,828, issued to A. Proulx on Jan. 5, 1993; and U.S. Pat. No. 5,599,447, issued to S. Pearl et al. on Feb. 4, 1997.

Throughout the conduct of the entire biopharmaceutical protein manufacturing process, those skilled in the art will see several opportunities in which viral contamination can occur. For example, during preparation of the broth, much of the raw materials may contain viruses. Also, ambient contamination is possible. During cell culture, introduction of gases provides another source of contamination. While steps are of course taken to prevent contamination, those skilled in the art will appreciate that the very conditions that support the growth of cellular components and production of target medium—such a warmth, and concentrated and readily accessible sources of nutrients—will support growth of viruses, rendering such fluids prone to contamination.

Typical viruses are identified in the following table:

| Name (Acronym) | ~Size (nm) | Shape | Natural Host |
|---|---|---|---|
| PP7 | 25 | Icosahedral | Bacteria |
| MS2 | 26 | Icosahedral | Bacteria |
| φX174 | 25–35 | Icosahedral | Bacteria |
| PR772 | 53 | Icosahedral | Bacteria |
| φ6 | 78 | Icosahedral | Bacteria |
| T1 | 50 × 150 | Icosahedral | Bacteria |
| Porcine Parvo (PPV) | 18–24 | Icosahedral | Pig |
| Canine Parvo (CPV) | 18–24 | Icosahedral | Dog |
| Minute Virus of Mice (MVM) | 18–26 | Icosahedral | Mouse |
| Human Parvo (B19) | 18–26 | Icosahedral | Human |
| Poliovirus Sabin 1 (Polio-I) | 25–30 | Icosahedral | Human |
| Encephalomyocarditis (EMCV) | 25–30 | Icosahedral | Mouse |
| Hepatitis A (HAV) | 27–32 | Icosahedral | Mammal |
| Hepatitis E (HEV) | 27–34 | Icosahedral | Mammal |
| Feline Calicivirus (FCV) | 30–38 | Icosahedral | Feline |
| TT Virus (TTV) | 30–50 | Unknown | Human |
| Hepatitis C (HCV) | 30–60 | Spherical | Mammal |
| Hepatitis D (HDV) | 35 | Spherical | Mammal |
| Hepatitis B (HBV) | 42 | Icosahedral | Mammal |
| Duck Hepatitis (DHBV) | 40–48 | Spherical | Duck |
| Simian Virus 40 (SV-40) | 40–50 | Icosahedral | Monkey |
| Japanese Encephalitis (JEV) | 40–50 | Spherical | Human |
| West Nile Virus (WNV) | 40–60 | Spherical | Human |
| Bovine Viral Diarrhea Virus (BVDV) | 50–70 | Spherical | Bovine |
| Sindbis (SIN) | 60–70 | Spherical | Human |
| Reovirus-3 (REO-3) | 60–80 | Spherical | Mammal |
| Adenovirus (ADV) | 70–90 | Icosahedral | Mammal |
| Vesicular Stomatitis Virus (VSV) | 70 × 175 | Bullet | Bovine |
| Murine Leukemia Virus (eMuLV; XMuLV) | 80–110 | Spherical | Mouse |
| Human T-Cell Leukemia Virus (HTLV) | 100 | Spherical | Mammal |
| Human Immunodeficiency Virus (HIV-1;-2) | 80–120 | Spherical | Mammal |
| Influenza A (INFA) | 80–120 | Helical | Mammal |
| Herpes Simplex (HSV) | 150–200 | Spherical | Mammal |
| Infectious Bovine Rhinotracheitis (IBR) | 150–200 | Spherical | Bovine |
| Bovine Herpes Virus (BHV) | 120–300 | Icosahedral | Bovine |
| Pseudorabies (PRV) | 120–200 | Spherical | Swine |
| Epstein Bar (EBV) | 120–200 | Spherical | Human |
| Cytomegalovirus (CMV) | 150–200 | Pleo-Spherical | Mammal |
| Parainfluenza (PI-3) | 150–300 | Pleo-Spherical | Mammal |
| Sendai (SEN) | 150–300 | Spherical | Mouse |
| Vaccina | 270 × 350 | Brick-Shaped | Mammal |

It is unlikely that a manufactured protein-containing solution will be prone to contamination by all of the above (and other) viruses. Those skilled in the art will know which one (or ones) would be the most likely candidate(s) for contamination based, for example, on the particular constituency of the solution on interest, and target accordingly with an appropriate membrane configuration.

Although the biopharmaceutical processes summarized herein are of particular interest, the present methodology can be employed for purification of manufactured protein-containing solutions produced by any cultured cell colony, even those not involving genetic manipulation on the molecular level, such as the common practice of harvesting of enzymes (insulin) from isolated and artificially-cultured cell lines.

As stated, the manufactured protein-containing solution is conducted through said filtration device under conditions sufficient to effect passage of said protein through each of said asymmetric membranes and out of said housing through said filtrate outlet, whereby a targeted virus contaminating said protein-containing solution—being substantially prevented from passage through said asymmetric membranes—is substantially removed therefrom. The method is conducted using heretofore unprecedented filtration parameter values for protein passage, flux, and viral retention.

In respect of protein passage, the method is conducted such that greater than approximately 98% of the protein solute in the upstream protein-containing solution is passed downstream of the asymmetric membranes enclosed in the filtration device. The low range of such percentage is generally applicable to high-resolution separations involving the most challenging types of protein-containing solutions, i.e., wherein the protein concentrations are comparatively high and the target contaminating virus is comparatively small.

In respect of flux, for protein-containing solutions wherein the target contaminating virus is comparatively large (i.e., in the order of about 75 nm), the method is conducted at a minimum flux of approximately 5 to approximately 20 lmh/psi. For protein-containing solutions wherein the target virus is comparatively small (i.e., in the order of about 30 nm), the method is conducted at a minimum flux of approximately 2 to approximately 4 lmh/psi. Flux is calculated herein as follows: Flux=(v/t·a)/p, wherein "v" is volume in liters, "t" is time in hours, "a" is membrane area in square meters, and "p" is transmembrane pressure in psi.

In respect of viral retention, the method is conducted such that the protein-containing solution is passed through the asymmetric membranes at a viral log reduction value of at least 3 (i.e., 99.9% retention), but in general, greater than 6 (i.e., 99.9999% retention). For purposes of the present invention, log retention value (i.e., LRV; the negative logarithm of the sieving coefficient) is determined according to the following formula: LRV=$-\log_{10}$ (1−R), wherein R is a value from 0 to 1 representing the empirically determined ratio of rejected virus. Since LRV is a function in part of particle size, a membrane will have different LRVs for different viruses.

The principal factors that have led to implementation of such unprecedented method performance parameters, in no particular order, are: membrane porosity, membrane morphology, membrane orientation, and membrane number.

In respect of membrane porosity, each of the membranes used for the method are configured with a porosity that would, if the membrane were to be used alone, would be considered "too loose" or "too leaky", and essentially unacceptable for the high viral retention requirements demanded by the biopharmaceutical industry. Accordingly, if isolated from the membrane group and examined for protein-containing solution filtration performance, an individual membrane may have a desirably high flux, but present an undesirably low viral LRV.

In respect of membrane morphology, each of the membranes used for the method are configured as asymmetric membranes. The details of and methods leading to such morphological configuration are described elsewhere herein. As to its function and contribution to the accomplishment of the inventive method, such asymmetry enables one to establish a relatively thin "tight" surface of small average pore size suitable for viral sieving, while having a comparatively "open" structure which can contribute to accomplishment of good flux. Hydraulic resistance is concentrated in the thin skin, and for membranes having the same average pore size, the skinned membrane will have higher flux than an isotropic membrane having similarly-sized pores throughout its surface. The asymmetry essentially functions to provide a suitable balance between the oft opposing objectives of viral retention and high flux.

It is not enough that the membranes be asymmetric. The retention-flux balance can sway unfavorably if the membranes are not properly oriented. Thus, in respect of membrane orientation, practice of the present invention requires that at least foremost of the asymmetric membranes used is oriented such that when fluid is introduced into the filtration device it impinges upon this membrane on it "open" sides. In other words, this foremost membrane is oriented with it "tight side downstream" (TSDS). Preferably, at least two adjacent asymmetric ultrafiltration membranes are oriented TSDS. And, even more preferably, all asymmetric ultrafiltration membranes employed are oriented TSDS.

This orientation is conducive to the accomplishment of good flux, because the "open" bulk of the membrane essentially acts as a pre-filter. In the opposing orientation, i.e., "tight side upstream" (TSUS), flow incident on the membrane immediately meets resistance on the "tight" surface, and is essentially "slowing" at the outset, due to plugging with any retained matter.

In NFF with the membrane skin facing the feed, the pressure drop across the membrane is larger than any lateral pressure drop that may occur due to flow variances or other instabilities that would cause lateral pressure drop across the face of the membrane and thereby lateral flow. Since more flow is going through the larger pores, the pressure at the entrance to the larger pores will be less than at the entrance to the smaller pores, and a lateral pressure drop will occur from the smaller to the larger. Particles at or near the membrane surface in this case will be moved with the flow and have a greater chance of "finding" a larger pore, and passing through the membrane.

For the case of membranes oriented TSDS, the porous support material of the membrane will serve as a hindrance to lateral flow by the particles, and thereby reduce the chance of the particle moving to a larger pore. This is especially important in the inventive methodology because multiple layers of membranes are employed. After passing through a layer, if the particle were to come directly in contact with the "tight side" of the subsequent layer, it may tend to flow laterally to a larger pore. When the subsequent layer is oriented "tight side down stream", the particle is retrained from lateral flow by the porous support material of the subsequent layer, through which the particle must pass before coming to the next retentive layer.

In practice, to optimize flux, it is—as stated above—preferable that all asymmetric membranes used in the filtration device be oriented with their "tight side downstream". However, where more than two asymmetric membranes are utilized, it is contemplated that one seeking to "fine tune" the flux-retention balance may want to employ an asymmetric membrane(s) oriented with its "tight side upstream". This could be done, for example, to improve log retention value in application wherein the removal of viral contaminants is of much higher concern than optimizing protein product yields. Regardless, even in embodiments wherein certain membranes are oriented "tight side up stream", it is felt that good flux is a central feature of the present invention and that the accomplishment thereof will always be an important part of the invention. As such, in all embodiments of the inventive method, the leading membrane—as stated above—is oriented with its "tight side down stream".

It will be appreciated that membrane porosity, morphology, and orientation, whilst effecting both retention and flux, are generally established with an eye towards optimizing, improving, or maintaining flux. The principal variable upon which good retention is accomplished is membrane number. As defined herein, the present invention calls for the use of at least two asymmetric membranes. While applicants do not wish to be bound to any theory used in explanation of the present invention, it is believed by using multiple membranes having the porosity, morphology, and orientation described above, a good balance between retention and flux can be established. Aside from the teaching herein, applicants are unaware of any membrane-based filtration process wherein such balance can be achieved by the use of a single membrane.

The number of membranes employed will depend on the constituency and configuration of the individual membranes. More "open" membranes will need to be used in greater numbers to accomplish the same the retention-flux balance than less "open" membranes. The number of membranes that one can use for the invention is not boundless. With too many membranes, logistical and practical problems such as thickness, material costs, bulk, and overall unworkability begin to emerge. The point at which this will occur will vary amongst applications. Regardless, those skilled in art, provided with the teaching herein, will be able to determine the appropriate numbers of membranes to use.

EXAMPLES

The following examples illustrate specific embodiments of the present invention representative of only a few possibilities of practicing within the full scope of the invention.

Example 1

Large Virus Removal

An ultrafiltration polymeric membrane suitable for the multi-layered virus removal method of the present invention was prepared and evaluated. (This membrane is an example of a high integrity ultrafiltration membrane.)

More particularly, the high-integrity ultrafiltration membranes were made by dissolving 17 to 22% by weight of Radel A 200, a polyethersulfone manufactured by Amoco Chemicals of Alpharetta, Ga., in a mixture of triethylene glycol ("TEG") and N-methylpyrrolidone ("NMP") in a ratio of TEG/NMP of 1.8. The solution was filtered and degassed. Upon heating, the cloud point of the solution was found to occur at 50° C. The solution was cast onto a 0.0015 inch thick Mylar belt passing over a casting drum submerged in water kept at 57° C. A coating knife was used to set the cast thickness to about 200 μm, with only about ½ inch of cast film exposed to dry air before the point of immersion in the water bath. The casting speed was 15 to 30 ft/min.

Formed membrane was extracted by passing the cast through additional water baths and dried using an impingement drier with air temperature controlled at about 70° C. The membrane was hydrophilized by passing it through a solution of Sartomer 9035, in accordance with the teaching of U.S. Pat. No. 4,618,533, issued to M. J. Steuck on Oct. 21, 1986.

Sartomer 9035 is an alkoxylated water-soluble triacrylate manufactured by Sartomer Chemical Co. of West Chester, Pa. The Sartomer 9035 monomer (3.0 wt %) is dissolved in a mixture of Igracure 2959 (0.25 wt %), acetone (2.0 wt %), hexylene glycol (4-methyl-2,4-pentanediol MPD) (25.0 wt %), and water (69.75 wt %). Igracure 2959 is 4-(2-hydroxyethoxy)phenyl-(2-hydroxy-2-propyl)-ketone and is available from Ciba Specialty Chemicals, Inc. (Tarrytown, N.Y.).

The membrane was fully wetted by the monomer solution, then exposed to UV radiation to form a polymeric hydrophilic coating cross-linked onto the surfaces of the membrane. After additional extraction in water and drying, an ultrafiltration membrane is recovered.

Single layer samples of such ultrafiltration membrane were evaluated and found to have a water permeability of 50 to 200 lmh/psi. Further, the sample membranes were found to have an isopropyl alcohol (IPA) automated ramp bubble point (ABP) greater than 89 psi when tested in TSDS orientation with a porometer manufactured by Porous Materials, Inc. of Ithaca, New York. For the ABP test method, the BP is registered at a sudden transition between low level "random, diffusion" bubbles that occur below the BP and a burst of bubbles that occur at the BP. This transition was found to be very clear in the sample membranes. FIG. 1 provides a scanning electron micrograph of a sample membrane.

The sample membranes were stacked and assembled into filtration devices in several and varying configurations. In all configurations, a sample membrane is present at least in the upstream layer, but in more favored ones, it is present in all layers of the filtration material. Further, the upstream layer was in all tested filtration device configuration in TSDS orientation, with following layer(s) in either TSDS or TSUS orientation. The several membrane configuration that were evaluated for virus removal performance included 2-layer devices (orientations: TSDS/TSDS, or TSDS/TSUS), 3-layer devices (orientations: TSDS/TSDS/TSDS, or TSDS/TSUS/TSDS, or TSDS/TSDS/TSUS, or TSDS/TSUS/TSUS) or more layers in similar arrangements, where the nomenclature in parentheses refers to orientation of individual layers with the upstream layer listed first.

Among the evaluated filtration devices, a 3-layer configuration (orientation: TSDS/TSDS/TSDS) was found to fully retain viruses, as consistently demonstrated by the absolute removal of bacteriophage φ6 (size 78 nm) when challenged with a suspension of at least 10 pfu/ml up to volumes of 50 ml/cm$^2$ of tested filter. There was no virus detected downstream of the 3-layer filter both in "buffer only" solutions, as well as protein-containing solutions having a 2.5 mg/ml of monoclonal IgG. IgG protein passage was found to be greater than 98%. Average processing flux in the presence of IgG was about 20 lmh/psi averaged over the full volume filtered (i.e., approximately 20 ml/cm$^2$).

The layers were in 47 mm disk form and were stacked in a housing represented by FIG. 2. No gluing or bonding of the layers of the present invention is necessary. The periphery of the filtration material must be secured, however, to insure fluid only flows through the membrane. The housing 26 contained the upstream layer 2, intermediate layer 4 and the third or downstream layer 6. To insure the fluid flowed in the inlet 35, through the membranes 37 and through the outlet 36, two o-rings 7 and 8 were employed in the housing.

This example represents large virus removal by the present invention and demonstrates substantial removal of large viruses is possible at a high processing flux with substantial passage of relatively large proteins, such as IgG. In comparison, a peer product currently available on the market, i.e., the aforementioned Pall DV50 product, achieves a low flux, and only 2 lmh/psi under similar conditions.

Example 2

Membranes were made according to the method described in Example 1, and subsequently pleated and incorporated into filtration cartridges. The cartridges each had an effective surface area of 4900 cm²

Each cartridge was challenged using 4 liters of φ6 virus suspension.

No virus was detected downstream of three cartridges tested.

The average processing flux was about 18 lmh/psi, which is in substantial agreement with the flux observed in testing flat stock membranes.

Full removal of φ6 virus was demonstrated in a pleated cartridge made with three layers (orientation TSDS/TSDS/TSDS) of the membrane, when challenged with a virus suspension of about $10^7$ pfu/ml.

Example 3

A regenerated cellulose composite membrane (sold as the Ultracel™ membrane by Millipore Corporation and found as catalog No. PLCXK) rated as 1000 kDa nominal molecular weight was used in a virus retention test in 1, 2, and 3 layers in TSDS, TSDS/TSDS, and TSDS/TSDS/TSDS orientation, respectively.

A model bacteriophage (size 28 nm) φX174 was used in Sorensen's buffer at a challenge level of about $10^7$ pfu/ml. Filtration was done at 10 psi and 250 ml of filtrate was collected from each 47 mm holder (cf., FIG. 2).

Flux and LRV were measured. Flux was only slightly lower than the water flux values estimated from known water permeability for this membrane. Table 1 below provides the results of testing the regenerated cellulose membrane with a number of layers.

TABLE 1

| Layers | Orientation | LRV of φX174 | Flux-lmh/psi |
|---|---|---|---|
| 1 | TSDS | 4.9 | 160 |
| 2 | TSDS/TSDS | >6.9 | 64 |
| 3 | TSDS/TSDS/TSDS | >6.9 | 48 |

Example 4

Small Virus Removal

Figure 3:
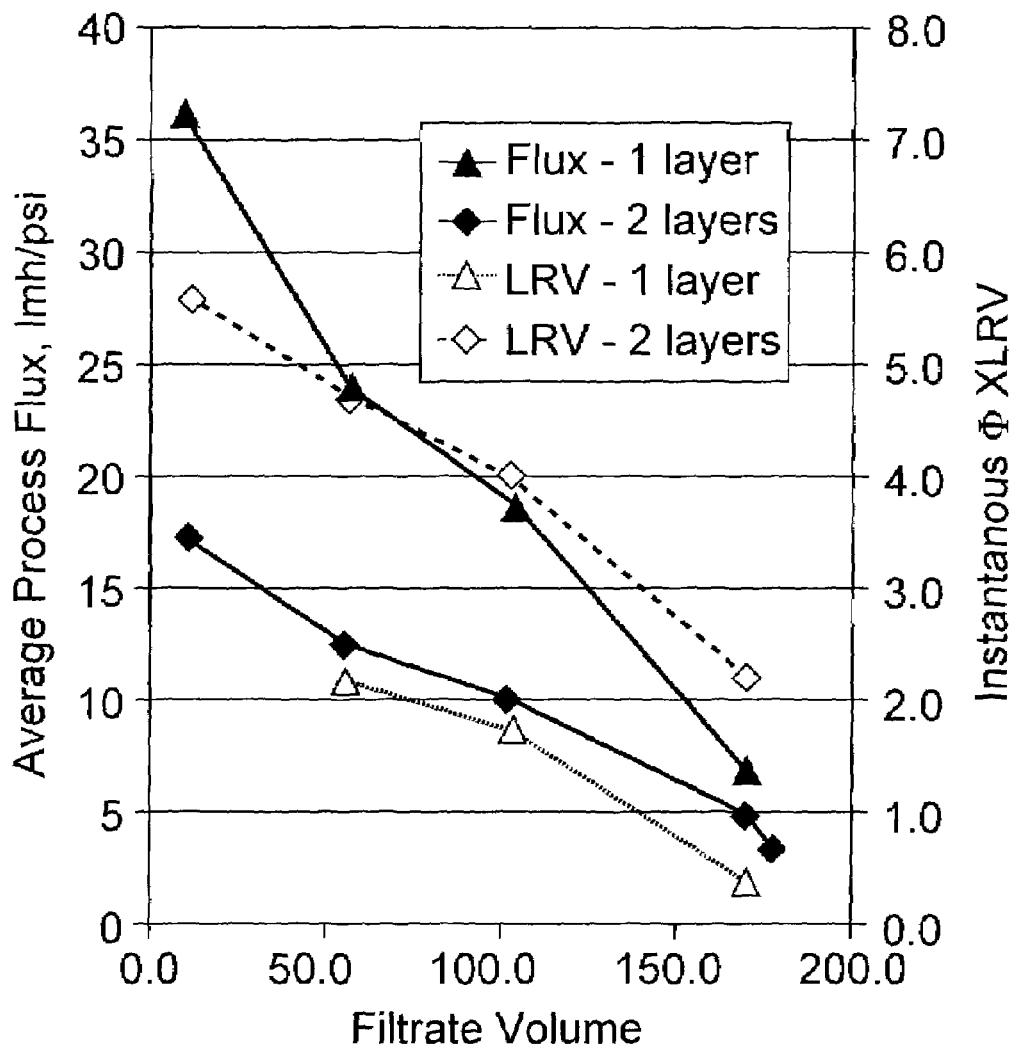
FIG. 3 is a graph that compares the flux and viral clearance (i.e., LRV) achieved using, on the one hand, a method according to an embodiment of the present invention (i.e., "2 layers" plots) and, on the other, a method according to the prior art (i.e., "1 layer" plots).

A 25 mg/ml solution of monoclonal antibody (MAb, molar mass approx. 160 kDa) in Tris-HCl buffer was spiked with model bacteriophage (size 28 nm) FX174 at a challenge level about $10^7$ pfu/ml. The solution was filtered at 30 psi through 47 mm disks of composite ultrafiltration membrane manufactured according to U.S. Pat. No. 5,017,292 and marketed under the trade name Viresolve™ by Millipore Corporation. A side-by-side comparison was done. One holder contained 1 membrane layer in TSDS orientation; another holder contained 2 membrane layers in TSDS/TSDS orientation. Filtrate volume, time, concentration of virus and monoclonal antibody in filtrate was measured several times during the filtration. Flux, virus LRV and MAb passage were calculated. FIG. 3 shows the resulting values of flux and virus LRV. The MAb passage (not shown in FIG. 3) was greater than 98% for all values measured at points corresponding to those in FIG. 3.

This example represents small virus removal by the present invention and demonstrates substantial removal of small viruses is possible at a high processing flux with substantial passage of relatively large proteins such as IgG. In comparison, a peer product currently available on the market, i.e., the aforementioned Pall DV20 product, achieves a low flux, and only 0.6 lmh/psi under similar conditions.

The invention claimed is:

1. A virus removal methodology, suitable for conducting a high-flux fluid separation of a virus from a protein in the course of biopharmaceutical manufacture, the methodology comprising the steps of:
   (a) providing a filtration device comprising a housing having a fluid inlet and a filtrate outlet, and containing at least two interfacially contiguous asymmetric membranes, wherein:
      (i) the asymmetric membranes are each substantially hydrophilic,
      (ii) at least two of the asymmetric membranes are each capable of substantially selectively preventing the passage therethrough of said virus and substantially permitting the passage therethrough of said protein,
      (iii) at least two of the asymmetric membranes have each a tight-side and an open-side, the average surface pore size of said tight-side being less than the average surface pore size of said open-side, and
      (iv) the foremost asymmetric membrane is oriented such that fluid introduced into said housing through the fluid inlet commences passage through said foremost asymmetric membrane through its open-side;
   (b) providing a manufactured protein-containing solution, wherein the predominant solute in said solution is said protein, and wherein the solution is prone to contamination by said virus; and
   (c) flowing said manufactured protein-containing solution through said filtration device using a normal flow filtration mode under conditions sufficient to effect substantial passage of said protein through each of said asymmetric membranes and out of said housing through said filtrate outlet, whereby any of said virus contaminating said manufactured protein-containing solution, being substantially prevented from passage through said asymmetric membranes, is substantially removed therefrom.

2. The virus removal methodology of claim 1, wherein the asymmetric membranes form a pleated tube.

3. The virus removal methodology of claim 1, wherein each of said asymmetric membranes are substantially identical in their composition and porosity, and wherein the porosity of each of said asymmetric membranes is defined to enable performance of the virus removal methodology, yielding a log reduction value (LRV) greater than 6 and a protein passage greater than 98%.

4. The virus removal methodology of claim 1, wherein the filtration device employed in said methodology is a filtration capsule comprising a tubular housing though which a fluid process stream can be conducted, the housing having said fluid inlet and said filtrate outlet, and containing a pleated tube compose of three interfacially-abutting asymmetric membranes, wherein the pleated tube is positioned within said process stream between said fluid inlet and said filtrate outlet.

* * * * *